United States Patent [19]

Moore

[11] Plant 4,480

[45] Nov. 13, 1979

[54] MINIATURE ROSE PLANT

[76] Inventor: Ralph S. Moore, 2519 E. Noble Ave., Visalia, Calif. 93277

[21] Appl. No.: 925,989

[22] Filed: Jul. 19, 1978

[51] Int. Cl.[2] ..... A01H 5/00

[52] U.S. Cl. ..... Plt./7

[58] Field of Search ..... Plt./7

*Primary Examiner*—Robert E. Bagwill

[57] ABSTRACT

The subject of the present described invention is a new and distinct variety of miniature rose plant characterized by small quite double flowers of a distinct lavender color with buds of formal hybrid tea (exhibition) shape, the color being a darker shade and the plant more vigorous than Lavender Lace.

1 Drawing Figure

1

The present invention relates to a new and distinct variety of hardy, dwarf, bush type rose plant of the miniature class; the variety being primarily characterized—as to novelty—by lavender buds and flowers which in general color effect are similar to Angel Face, Floribunda (U.S. Plant Pat. No. 2,792).

The variety is further characterized by:

An abundance of bloom, with flowers borne singly or several to the stem in loose clusters.

Little or no fragrance.

A plant which is vigorous, of rounded bushy shape with semi-glossy, small foliage with pointed leaflets; the buds and flowers being similar in form and size to Lavender Lace (miniature — U.S. Plant Pat. No. 2,991).

The plant, which has a normal height of 10 inches or more, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at my nursery located at Visalia, Calif., under conditions of careful control and observation, as a cross between Little Chief, miniature (not patented) as the seed parent and Angel Face, Floribunda (U.S. Plant Pat. No. 2,792) as the pollen parent.

Subsequent to origination of the variety I successfully asexually repoduced it, in my nursery located as aforesaid, by budding as well as by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bushy; rounded; seedling; greenhouse; outdoors; cut flowers; garden decoration; potted plant.

Class: Miniature. Variety name: Lavender Jewel.

Flowers borne: Singly and several together (3 to 5) on slender wirey stems.

Quantity of bloom: Abundant both outside and in greenhouse.

Bud:

2

*Peduncle.*—Medium length; slender but sturdy; erect; medium green, sometimes tinted bronze (outdoors); hairs — few short.

*Before calyx breaks.*—Size — small. Form slender — ovoid: pointed with few foliaceous appendages and few or no hairs on surface of bud; with foliaceous parts extending beyond the tip of the bud equal to less than one-half of its length. Color — medium green, occasionally tinted with bronze (outdoors).

*As calyx breaks.*—Color — lavender — near Magnolia Purple 030/1 (usually lighter shade on lower half of petal — near Magnolia Purple 030/2. Opening: opens well in all weather.

Bloom:

*Size when fully open.*—Small, averaging about 35 mm.

*Petalage.*—Double — averaging about 50 petals, arranged regularly plus sometimes several small petaloids.

*Form.*—Cupped or flat at first, becoming more high centered, with petals rolled loosely outward, and later at maturity full with petals often folded at edge to give a pointed effect and rolled loosely outward and downward. Open flower full, rounded, sometimes may show stamens.

Petals: Fairly thick; satiny on inside and on outside surface.

*Shape.*—Outside petals, broad lanceolate with rounded tip; intermediate — broad lanceolate with rounded tip; inside — lanceolate with short acute tip.

Color: Newly opened flower from a plant grown in plastic greenhouse (July 1978), Visalia, Calif.

*Outside petal.*—Outside surface — near Magnolia Purple 030/1 becoming lighter color toward base. Inside surface — near Magnolia Purple 030/1 becoming lighter color on lower $\frac{2}{3}$ to $\frac{1}{2}$ of petal, with small yellowish area at base.

*Intermediate petal.*—Outside surface — similar to outside petal. Inside surface — similar to outside petal.

*Inner petal.*—Outside surface — same as intermediate petal; inside surface — same as intermediate petal.

*General color effect.*—Newly opened flowers — clear shade of mauve (lavender) — with reddish undertone. Three days open — color similar to newly opened flowers. Behavior — opens well in all weather. Color better than most other mauve (lavender) miniatures. Spent petals drop off. Flower longevity (June 1978) — plant in pot 6–8 days or longer. Cut flowers at living room temperature 3–5 days.

Reproductive Organs:

*Stamens.*—Moderate number, arranged regularly about pistils.

*Filaments.*—Varying length, short, yellow.

*Anthers.*—Well formed; yellow.

*Pollen.*—Moderate amount.

*Pistils.*—Average number.

*Styles.*—Fairly even; short length; bunched; color — reddish.

*Ovaries.*—All enclosed in calyx.

*Hips.*—None.

*Sepals.*—Permanent; spear shaped; recurved.

*Seed.*—None.

Foliage:

*Leaves.*—Compound of five (sometimes three) leaflets; small; leathery; semi-glossy.

*Leaflets.*—Shape: broad, nearly oval; apex acute; base rounded or rounded acute. Margin serrate. Color: medium green; new growth — reddish. Rachis: medium strength; upper side may have a few tiny short prickles or hairs, grooved; underside sparsely thorny with few or no tiny prickles.

*Stipules.*—Medium long; medium width; short to medium narrow points which turn out usually at about 45 degrees.

Growth:

*Habit.*—Dwarf; bushy; rounded; much branched.

*Growth.*—Free vigorous; internodes short.

*Canes.*—Medium; slender; sturdy.

*Main stems.*—Color: medium green.

*Thorns.*—Average; slender; hooked sightly downward; color; brown. Prickles — none. Hairs: none.

*Branches.*—Color: medium green. Thorns: few; short length; slender; nearly straight. Medium to short oval base. Prickles: none. Hairs: none.

The miniature rose plant and its flowers as herein decribed may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, rounded much branched habit, substantially as illustrated and described, characterized by buds and flowers which are (A) medium to deep mauve-lavender in color (similar to the pollen parent 'Angel Face' — U.S. Plant Pat. No. 2,792), the bud and flower resembling 'Lavender Lace' miniature, U.S. Plant Pat. No. 2,991, in size and shape; and (B) further characterized by a plant which is vigorous and compact, easy to propagate from cuttings or by budding, with an abundance of small size semi-glossy foliage and an abundance of flowers borne singly or several to the stem in loose clusters.

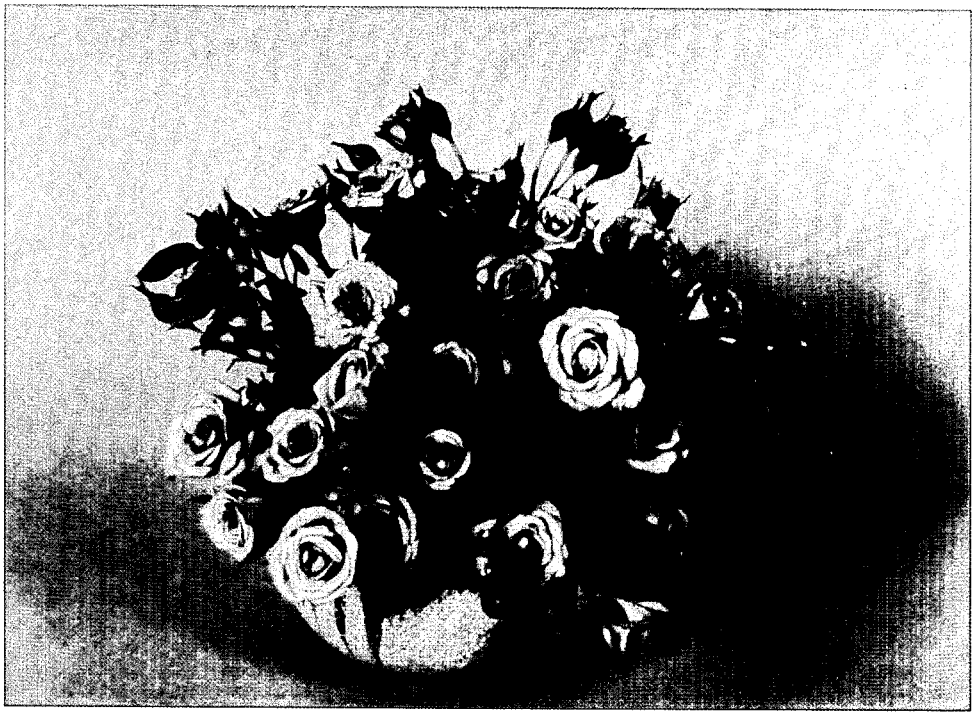

* * * * *